United States Patent [19]

Bey et al.

[11] Patent Number: 4,916,151

[45] Date of Patent: Apr. 10, 1990

[54] METHOD OF TREATING PARKINSON'S SYNDROME

[75] Inventors: Philippe Bey; Michael G. Palfreyman, both of Cincinnati; Ian A. McDonald, Loveland, all of Ohio

[73] Assignee: Merrell Dow Pharmaceuticals Inc., Cincinnati, Ohio

[21] Appl. No.: 323,071

[22] Filed: Mar. 10, 1989

Related U.S. Application Data

[63] Continuation of Ser. No. 143,549, Jan. 13, 1988, abandoned, which is a continuation-in-part of Ser. No. 806,162, Dec. 5, 1985, abandoned.

[51] Int. Cl.$^4$ .................. A61K 31/40; A61K 31/135; A61K 31/195

[52] U.S. Cl. .................................... 514/419; 514/561; 514/649

[58] Field of Search ........................ 514/419, 561, 649

*Primary Examiner*—Stanley J. Friedman

[57] ABSTRACT

Novel nonaromatic fluoroallylamines are potent MAO inhibitors and at low dose selectively inhibit MAO-B. They are useful in the treatment of depression and co-administration with L-dopa and decarboxylase inhibitors, in the treatment of Parkinsonism.

9 Claims, No Drawings

METHOD OF TREATING PARKINSON'S SYNDROME

CROSS-REFERENCE TO RELATED APPLICATION

This is a continuation of application Ser. No. 143,549, filed Jan. 13, 1988, which is a continuation-in-part of application Ser. No. 806,162, filed Dec. 5, 1985, both now abandoned.

BACKGROUND OF THE INVENTION

This invention relates to novel chemical compounds and to methods of treatment employing these compounds.

The class of compounds known as monoamine oxidase inhibitors (MAO inhibitors) has been employed in psychiatry for over twenty years for the treatment of depression [See Goodman and Gilman, *The Pharmacological Basis of Therapeutics*, 6th Ed., McMillan Publishing Co., Inc., N.Y., 1980, pages 427–430]. MAO inhibitors currently used in the United States for treating depression are tranylcypromine (PARNATE®, SKF) phenelzine (NARDIL®, Park Davis), and isocarboxazid (MARPLAN®, Roche). In addition, another MAO inhibitor, pargyline (EUTRON®, Abbot), is available for the treatment of hypertension [See *Physicians' Desk Reference*, 34th Ed., Medical Economics Co., Oradell, N.J., 1980, pages 1327–1328 (phenelzine), pages 1466–1468 (isocarboxazid), pages 1628–1630 (tranylcypromine), and pages 521–522 (pargyline)]. In addition to being used in treating depression, MAO inhibitors can be employed to treat other psychiatric disorders, such as phobic anxiety states.

Parkinson's syndrome is characterized by low levels of dopamine in the brain. The disease can be treated by the administration of exogenous dopa (or preferably L-dopa) which passes through the blood-brain barrier into the brain where it is transformed to dopamine which replenishes the endogenous monoamine. Dopamine is itself not effective for treating Parkinson's syndrome since it is not transported across the blood-brain barrier. It is known that the co-administration of a peripherally active aromatic amino acid decarboxylase (AADC) inhibitor (such as carbidopa or benserazide) with L-dopa potentiates the effect of L-dopa and provides effective therapy at a lower dose of L-dopa. (see *Physician's Desk Reference*, Medical Economics Co.,Oradell, N.J. p. 1198–1199). The potentiation of L-dopa occurs because the AADC inhibitor prevents the peripheral decarboxylation of L-dopa thereby increasing the amount of circulating L-dopa available for absorption into the brain. Prevention of the peripheral decarboxylation of dopa will also decrease the amount of circulating dopamine which is responsible for undesirable side effects. It is also known that the co-administration of certain MAO inhibitors (such as L-deprenyl) with L-dopa potentiates the effect of L-dopa and also provides effective therapy at a lower dose of L-dopa because the MAO inhibitor prevents the oxidative deamination of dopamine upon its formation from L-dopa.

It is believed that the MAO inhibitors act to alleviate psychiatric disorders, such as depression, by increasing the concentration of one or more biogenic monoamines in the brain or sympathetic nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked, and the result is an increase in the availability of the monoamines for their physiological functions. Among the physiologically active monoamines which are known substrates for MAO are: (a) the so-called "neurotransmitter" monoamines, such as the catecholamines (e.g. dopamine, epinephrine, and norepinephrine) and the indoleamines (e.g. tryptamine and 5-hydroxytryptamine), (b) the so-called "trace" amines (e.g. o-tyramine, phenethylamine, tele-N-methylhistamine), and (c) tyramine.

The usefulness of the MAO inhibitors in treating depression is limited because the administration of such agents can potentiate the pharmacological actions of certain food substances or drugs leading to dangerous and sometimes lethal effects. For example, persons receiving a MAO inhibitor must avoid the ingestion of foods which have a high tyramine content (such as cheese) because the MAO inhibitor will block the metabolic degradation of tyramine in the gut to produce high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy cannot be given directly-acting sympathomimetic drugs (or precursors thereof) which are themselves substrates for MAO (e.g. dopamine, epinephrine, norepinephrine, or L-dopa) or indirectly-acting sympathomimetic drugs (e.g. amphetamines or cold, hay-fever, or weight control preparations that contain a vasoconstrictor). The potentiation of the pressor effect of indirectly-acting sympathomimetic drugs is especially profound. This is because such drugs act peripherally primarily by releasing catecholamines in nerve endings, and the concentration of the liberated catecholamines will be dangerously elevated if the metabolic degradation of the catecholamines via MAO is blocked.

Biochemical and pharmacological studies indicate that the MAO enzyme exists in two forms known as "MAO Type A" (MAO-A) and "MAO Type B" (MAO-B). The two forms differ in their distribution in body organs, in their substrate specificity, and in their sensitivity to inhibitors. In general, MAO-A selectively oxidizes the so-called "neurotransmitter" monoamines (epinephrine, norepinephrine and 5-hydroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus they can be preferentially inhibited depending upon the chemical structure of the inhibitor and/or the relative concentrations of the inhibitor and the enzyme. The MAO inhibitors currently sold in the United States for the therapy of depression (tranylcypromine, phenelzine, and isocarboxazid) are not preferential in their action upon MAO. However, various chemical compounds are known in the art to be preferential inhibitors of MAO, the most important being clorgyline, pargyline, and L-deprenyl which are all reported to be clinically effective antidepressant agents.

MAO-A is preferentially inhibited by clorgyline, while MAO-B is preferentially inhibited by pargyline and L-deprenyl. The selectivity of an inhibitor for MAO-A or MAO-B in vivo will be dose-dependent, selectivity being lost as the dosage is increased. Clorgyline, pargyline, and L-deprenyl are selective inhibitors at lower dosages, but are less selective inhibitors as higher dosages. The literature concerning MAO-A and MAO-B and the selective inhibition thereof is extensive [See, for example, Goodman and Gilman, ibid, pages 204–205; Neff et al., *Life Sciences*, 14, 2061 (1974); Murphy, *Biochemical Pharmacology*, 27, 1889 (1978); Knoll, Chapter 10, pages 151–171 and Sandler, Chapter 11, pages 173–181, in *Enzyme Inhibitors as Drugs*, M. Sandler, Ed., McMillan Press Ltd., London 1980; Lipper et al., Psychopharmacology, 62, 123 (1979); Mann et al., Life Sciences, 26, 877 (1980); and various articles in Monoamines Oxidase: Structure, Function, and Altered Functions, T. Singer et al. Ed., Academic Press. N.Y., 1979].

Of the selective inhibitors of MAO, L-deprenyl is of interest since the "cheese effect" is not observed at the low dosages where preferential inhibition of MAO-B occurs [See Knoll, *TINS*, pages 111–113, May 1979]. This observation is not unexpected since the intestinal mucosa contains predominantly MAO-A which, because it is not inhibited, permits oxidation and removal of the ingested tyramine. The selectivity of L-deprenyl for MAO-B may account for its ability to potentiate L-dopa for the treatment of Parkinson's disease without producing peripheral side effects, such as hypertension due to potentiation of pressor catecholamines [See Lees et al., Lancet, pages 791–795, Oct. 15, 1977 and Birkmeyer Lancet, pages 439–443, Feb. 26, 1977].

Previously the presence of an aryl moiety was believed necessary for potent MAO inhibition in those compounds which structurally mimic phenylethylamine, serotonin, the catecholamines, indoleamines, and trace amines such as the arylalkylhydrazines, propargylamines, phenylcyclopropylamines, and methyltryptamines. Applicants have discovered a class of potent MAO inhibitors which do not structurally mimic the natural monoamines. In many cases, these novel, nonaromatic MAO inhibitors selectively inhibit MAO-B at low doses.

SUMMARY OF THE INVENTION

Fluoroallylamines of formula 1

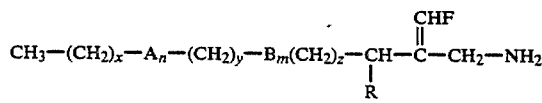

wherein
R is hydrogen or a $(C_1-C_4)$alkyl;
n and m are each zero or 1;
A and B are each selected from

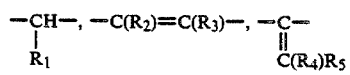

$x+y+z$ is 0 to 16 but y is not 0 when n and m are both 1 and y must be greater than 2 when A and B are selected from O, S and $SO_2$;

$R_1$, $R_2$, $R_3$, $R_4$ and $R_5$ are each a hydrogen or a $C_1-C_4$ alkyl or a pharmaceutical acceptable acid addition salt thereof are potent MAO inhibitors and are useful in the treatment of Parkinson's and related syndromes and of depression.

DETAILED DESCRIPTION OF THE INVENTION

As used herein the term alkyl group means both straight- and branched- chain alkyl group. $(C_1-C_4)$ alkyl groups are methyl, ethyl, propyl, isopropyl, n-butyl, isobutyl, and tert butyl.

It will be apparent to those skilled in the art that, because the compounds of formula 1 contain one or more double bonds, geometric isomerism is possible. It should be understood, therefore, that in formula 1 the fluorine atom on the allylamine double bond can be oriented in the cis position or in the trans position. In naming compounds of formula 1 herein, the prefixes "(E)" and "(Z)" are used in the conventional manner to indicate the stereochemistry at the allylic double bond. If no stereochemical designation is given, both the substantially pure isomers, or mixtures thereof, are meant.

The primary nitrogen of the allyl amine group can be substituted with a $(C_1-C_4)$ alkyl group. These secondary amines are considered to be equivalent to the unsubstituted primary amines of formula 1. The substituted compounds can be prepared by conventional N-alkylation methods. For example, the N-ethyl derivatives can be made by treating the primary amine with benzaldehyde in a lower alcohol (e.g. ethanol) to form the Schiff base, treating the Schiff base with triethyloxonium tetrafluoroborate, and hydrolyzing the intermediate thus formed.

The expression "pharmaceutically acceptable acid addition salts" is intended to apply to any non-toxic organic or inorganic acid addition salts of the base compounds represented by formula 1. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or a substantially anhydrous form. In general, the acid addition salts of these compounds are crystalline materials which are soluble in water and various hydrophilic organic solvents and which, in comparison to their free base form, generally demonstrate higher melting points and an increased chemical stability. Illustrative examples of the compounds of formula 1 are:

2-isobutyl-3-fluoroallylamine,
2-isopropyl-3-fluoroallylamine,
2-(9-octadecenyl)-3-fluoroallylamine,
2-(3-methyl-3-butenyl)-3-fluoroallylamine,
2-(4-methoxy-2-butenyl)-3-fluoroallylamine,
2-isobutylsulfonylmethyl-3-fluoroallylamine,
2-sec-butyl-3-fluoroallylamine,
2-butyl-3-fluoroallylamine,
2-hexyl-3-fluoroallylamine, 2-heptyl-3-fluoroallylamine,
2-ethoxymethyl-3-fluoroallylamine, and
2-thioethoxymethyl-3-fluoroallylamine, Preferred compounds of this invention are those formula 1 compounds wherein n and m are both zero, or wherein n and z are both zero and m is one with B being oxygen or sulfur. Also preferred are those formula 1 compounds wherein x+y+z is 0 to 4 and those compounds wherein R is hydrogen or methyl. The preferred compound of this invention is 2-isobutyl-3-fluoroallylamine, more preferably its "E" isomer.

The compounds of formula 1 can be prepared by a variety of procedures readily apparent to those skilled in the art. For example the compounds of formula 1 wherein z≠0 can be prepared in a manner analogous to that described in U.S. Pat. No. 4,454,158 or in McDonald, et al., *J. Med. Chem.*, 28, 186 (1985). The compounds of formula 1 wherein z=0 and B is O, S or $SO_2$ can be prepared in a manner analogous to that described in European Patent Application No. 85108443.3 and in I. McDonald and P. Bey, *Tet. Letters*, 26, 3807 (1985).

In practice the compounds of this invention wherein z≠0 are prepared by first preparing formula 2 diester

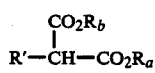      2 wherein
R' is $CH_3$—$(CH_2)_x$—$A_n$—$(CH_2)_y$—$B_m$—$(CH_2)_z$—CHR— or its functional equivalent
$R_a$ is tert-butyl, benzyl, diphenylmethyl, or triphenylmethyl; and
$R_b$ is a ($C_1$–$C_4$) alkyl, benzyl, diphenylmethyl or triphenylmethyl.

This diester is then treated with a strong base. The strong base must be non-nucleophilic and of sufficient strength to remove the proton on the methine moiety adjacent to the carboxy groups. Suitable bases are known in the art. Examples are (a) an alkyl lithium (e.g. n-butyllithium), (b) an aryl lithium (e.g. phenyllithium), (c) a lithium dialkylamide (e.g. lithium diisopropylamide), (d) sodium of lithium amide, (e) a metal hydride (e.g. sodium or potassium hydride), (f) metal alcoholate (e.g. sodium or potassium tert-butoxide), or (g) lithium or dilithium acetylide. The reaction between the diester and the base can be performed in an aprotic organic solvent (such as tetrahydrofuran (THF), diethyl ether, dimethylformamide (DMF), dimethyl sulfoxide (DMSO), dimethoxyethane, or dioxane, or mixtures thereof), using a temperature range of about 0° to 70° C., preferably room temperature, and a reaction time of about 5 minutes to 2 hours. Preferred bases for forming the carbanion are sodium hydride in dimethoxyethane, potassium tert-butoxide/n-butyllithium in THF, or sodium tert-butoxide in THF.

By the term, a functional equivalent of $CH_3$—$(CH_2)_x$—$A_n$—$(CH_2)_y$—$B_m$—$(CH_2)_z$—CHR— is meant a group which can be converted to a chain with the desired values of x, y, z, n, m, A and B. A functional equivalent can be used to prepare any of the formula 1 compounds but is most advantageously used where a desired value of x, y, z, n, m, A or B would interfere with the various reactions necessary to construct the fluoroallylamine moiety. The use of such functional equivalents will be readily apparent to those skilled in the art and will be exemplified below.

The anions of the formula 2 diesters are then treated with a halomethylating agent such as $CHClF_2$, $CHBrF_2$ and $CHF_2I$. The halomethylation of the carbanion of a formula 2 diester can be carried out in situ by adding the appropriate halomethylating agent to the anion at a temperature range of about 0° to 70° C. and allowing the reaction to proceed for about 1 to 24 hours, preferably about 1–2 hours. Depending upon the reactivity of the reactants, the halomethylating agent can be introduced at a higher temperature (about 40° C.), and the reaction mixture can be allowed to cool to room temperature to complete the reaction or the halomethylating agent can be introduced at room temperature.

The resulting fluorinated diester of formula 3

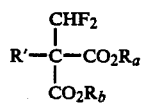      3 wherein R', $R_a$ and $R_b$ are as defined above is then cleaved by acid hydrolysis or by catalytic hydrogenation to convert either one or both of the ester groups (—$COOR_a$ or —$COOR_b$) to a free carboxylic acid group. Whether cleavage of one or both ester groups occurs will depend upon the nature of each ester group and the conditions employed for the cleavage reaction. In order to effect cleavage of only one ester group, it is preferred that the diester be mixed, the groups defined by $R_a$ and $R_b$ being chosen so that the ester group —$COOR_a$ can be selectively cleaved without cleaving the ester group —$COOR_b$. The selection of particular ester groups which can be selectively cleaved and methods for performing the selective cleavage will be apparent to those skilled in the art. To accomplish selective cleavage of the diester, it is preferred to employ a mixed diester wherein $R_a$ is tert-butyl, benzyl, diphenylmethyl, or triphenylmethyl and $R_b$ is a straight-chain ($C_1$–$C_4$) alkyl group (such as methyl, ethyl, propyl, or n-butyl).

The ester group defined by —$COOR_a$ can be selectively hydrolyzed by treatment with an organic or inorganic acid, either with or without an added solvent, using a temperature range of about 0° to 25° C., and a reaction time of about 1 to 10 hours. Ambient temperature is preferred. The choice of the acid for the hydrolysis is not critical, except that the acid should be chosen so that it can be easily removed after the hydrolysis stage. Trifluoroacetic acid is preferred since its low boiling point permits it to be easily removed from the hydrolysis product. When $R_a$ is benzyl, diphenylmethyl, or triphenylmethyl and $R_b$ is a straight-chain ($C_1$–$C_4$) alkyl group, the ester group —$COOR_a$ can also be selectively cleaved by subjecting the mixed diester to catalytic hydrogenolysis using conventional procedures, for example, by treatment under a hydrogen atmosphere in the presence of a catalyst (e.g. Pd/C) at ambient temperature for 1 to 48 hours. As will be apparent to those skilled in the art, the ester groups can be chosen so that both groups can be cleaved simultaneously by acid hydrolysis or catalytic hydrogenolysis. Thus, when it is desired to cleave both ester groups simultaneously, each of $R_a$ and $R_b$ should be a tert-butyl, benzyl, diphenyl, or triphenylmethyl group.

The resulting acid obtained by cleavage of the diester (either a diacid or a mixed acid-ester) is treated with a base whereby the acid undergoes decarboxylation and elimination of halide ion to afford the acrylic acid or the acrylate ester of formula 4

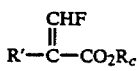   4 wherein R' is as defined above and $R_c$ is a hydrogen or a ($C_1$–$C_4$) alkyl. Whether the product is an ester ($R_c$ is a straight-chain $C_1$–$C_4$ alkyl group) or an acid ($R_c$ is hydrogen) depends upon whether the cleavage reaction in the first stage was performed selectively or nonselectively. The reaction can be performed using an aqueous or non-aqueous solvent. Strong bases, such as sodium hydroxide and the like, or weak bases, such as triethylamine or sodium bicarbonate, can be used. However, with strong bases, care must be taken to avoid using an excess of base to avoid interaction with the double bond. Weak bases (which do not interact with the double bond) can be used in excess. The choice of a particular base, the reaction solvent, and reaction conditions will be apparent to those skilled in the art. A preferred procedure is to employ aqueous sodium hydroxide in THF at ambient temperature. In general, a temperature range of about 0° to 25° C. and reaction time of 15 minutes to 2 hours can be used.

The acrylic acid or acrylate ester of formula 4 is reduced to yield the allyl alcohol of formula 5.

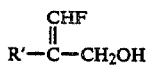   5 wherein R' is as defined above. The reducing agent employed for this transformation can be any reagent which is known in the art to be capable of selectively reducing an ester function or carboxylic acid function to the corresponding carbinol in the presence of a double bond. A preferred reducing agent is diisobutylaluminum hydride (DIBAL-H®) in hexane, THF, diethyl ether, or dichloromethane, or mixtures thereof. In a preferred procedure, a solution of the acrylate methyl ester in THF is cooled to about 0° to −78° C. (preferably −60° to −79° C.), the DIBAL-H® dissolved in hexane is added, and the temperature of the mixture is allowed to rise to ambient. The reaction time can be about 2 to 24 hours.

The allyl alcohol of formula 5 can be converted to the desired allyl primary amine using procedures known in the art to be useful for replacing an allylic hydroxyl group by an allylic primary amino group. A preferred laboratory method involves the direct formation of an imido derivative of formula 6

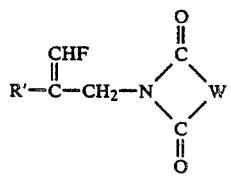   6 wherein R' is as defined above and W is

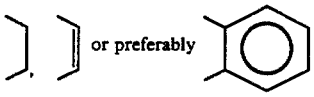

and subsequent cleavage of the imido group to generate the primary amino group.

The formula 6 imido group can be conveniently prepared by treating the formula 7 allyl alcohol with the appropriate imide (i.e., phthalimide, succinimide, or maleimide) in the presence of a triarylphosphine (e.g. triphenylphosphine) or a trialkylphosphine and diethyl azodicarboxylate in an aprotic organic solvent (e.g. THF or dioxane). The reaction can be performed using a temperature range of about 0° to 70° C. and a reaction time of about 1 to 24 hours. Ambient temperature is preferred. Subsequently the imido derivatives of structure 8 can be cleaved, preferably by reaction with hydrazine in an organic solvent, such as an alkanol (e.g. ethanol), at reflux temperature (50° to 100° C.) and a reaction time of about 30 minutes to 10 hours. It is preferable to add an acid (e.g. hydrochloric acid) after the hydrazine treatment to convert the product to the acid addition salt. Other reagents can be used to cleave the imido function. For example, the imide can be heated with a strong mineral acid (e.g. hydrochloric or sulfuric acid) or a mixture of hydrochloric acid and acetic acid. Acids, such as hydrobromic acid, which are reactive towards olefins usually cannot be used. The final products of structure 1 are conveniently purified and isolated as the acid addition salt using conventional purification methods.

In those instances wherein B is a O, $SO_2$ group and wherein z is zero, R' is preferably a functional equivalent such as a halomethyl group, for example, chloromethyl or bromomethyl. The formula 6 imido derivative wherein R' is a halomethyl group can advantageously be converted to the desired chain having the desired values of x, y, z, n, m, A and B at this stage by forming the appropriate alkoxide or thiolate anion and allowing this anion to react with the formula 6 compounds wherein R' is a halomethyl. Where it is desired that B have the value $SO_2$, oxidation of the corresponding compound wherein B is a sulfur atom is an alternate method of preparation.

The allyl alcohol of formula 5 can also be converted to the allyl primary amine via formation of the reactive intermediate of formula 7

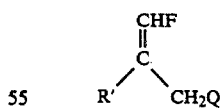   7 wherein R' is as defined above and Q is chlorine, bromine, iodine, benzenesulfonyloxy, p-toluenesulfonyloxy (tosyloxy), methylsulfonyloxy (mesyloxy), or other good leaving group, in which the —OH group is replaced by a leaving group, Q. Suitable leaving groups are known in the art. For example, chlorine, bromine, iodine, tosyloxy, or mesyloxy can be employed. Methods for replacing the hydroxy group by the leaving group are known in the art. For example, the allyl alcohol of formula 5 can be treated with a phosphorus trihalide (e.g. $PCl_3$ or $PBr_3$) in an organic solvent, such as toluene or benzene, to introduce halogen (e.g. chlorine or bromine). The allyl alcohol can also be treated with a tosyl halide or mesyl halide (e.g. tosyl chloride or mesyl chloride) in the presence of a base (e.g. pyridine) to introduce the tosyloxy or mesyloxy group. The reactive intermediate of formula 7 can be converted to the allyl primary amine of formula 8 in a known manner by displacement of the leaving group (Q) either directly by ammonia or by a nucleophilic group (B) which can then be cleaved to generate the primary amino group. Examples of groups defined by B which can be used to generate a primary amino group are the hexamethylenetetrammonium group, an imido group (e.g. phthalimido, succinimido, or maleimido group) or an alkylcarboxyamino group of the formula:

—NHCO$_2$R$_d$ wherein R$_d$, is (C$_1$–C$_4$)alkyl. The hexamethylenetetrammonium group can be introduced by treating the reactive intermediate of formula 7 with hexamethylenetetramine in an organic solvent (e.g. a (C$_1$–C$_4$)alkanol or chloroform) using ambient temperature and a reaction time of about 30 minutes to 24 hours. The hexamethylenetetrammonium group can be cleaved to generate the primary amino group by treatment with an aqueous acid (e.g. hydrochloric acid) under reflux. Acids which are reactive to the double bond cannot be used. The imido group can be introduced by treating the reactive intermediate of formula 7 with the appropriate alkali metal imide (e.g. sodium or potassium phthalimide, succinimide, or maleimide) in an organic solvent, such as tetrahydrofuran (THF), dimethylformamide (DMF), dimethylsulfoxide (DMSO), or dioxane using a temperature range of about 0° to 70° C., preferably ambient temperature, and a reaction time of about 30 minutes to 12 hours, preferably, 3 hours. The imido group can be cleaved to generate the primary amino compound of formula 8

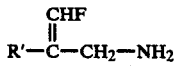

wherein R' is as defined above
using the methods described supra with respect to the cleavage of the formula 6 compounds.

The alkylcarboxyamino group (—NHCO$_2$R$_d$) can be introduced by treating the reactive intermediate with an alkali metal cyanate (e.g. sodium or potassium cyanate) and a (C$_1$–C$_4$)alkanol using a temperature range of about 70° to 150° C., preferably 100° C., and a reaction time of about 1 to 6 hours, preferably 2 hours. The alkylcarboxyamino group can be cleaved to generate the primary amino group by treatment with iodotrimethylsilane followed by hydrolysis. The reaction with iodotrimethylsilane is performed in an organic solvent (e.g. chloroform) using a temperature range of about 0° to 100° C., preferably 50° C., and a reaction time of about 1 to 24 hours, preferably 1 to 2 hours.

It should be apparent that the above-described decarboxylation and halide ion elimination from the diacid or mixed acid ester derivative of a formula 3 compounds gives a formula 4 acrylic acid or ester having geometric isomerism about the resulting allylic carbon-carbon double bond. Substantially, all of the product is that geometric isomer in which the fluorine located on the double bond is cis to the group represented by R'. When the other geometric isomer is desired, the above-described procedure is used to prepare the formula 6 imido derivative wherein the fluorine and R' group are cis to one another, and subsequently halogenating the double bond followed by a dehalogenation to reintroduce the double bond but wherein the fluorine and R' group are trans to one another. This isometric conversion can be performed by, for example, reacting the cis formula 6 compound with bromine in methylene chloride in the absence of light followed by a debromination using potassium iodide in acetone. The resulting trans formula 6 compound can be converted to the desired formula 8 compound as described above.

It should also be readily apparent that in those compounds wherein A or B contain an olefinic bond, this bond will be isomerized at the same time as will the olefinic bond of the allyl moiety. A suitable reactive equivalent, R' for a formula 1 compound wherein A or B contains an olefinic bond and wherein the allylic double bond is to be isomerized, is that value of A or B wherein the olefinic bond is of the opposite configuration to that of the desired compound. Thus the bond isomerization procedure will cause concurrent isomerization about both double bonds. Alternatively the reactive equivalent, R', will contain a functional protecting group for the olefinic bond of the A or B group. Olefinic functional group protection is well known to those skilled in the art.

The diesters of formula 2 are either known compounds or they can be prepared from known compounds using known methods or obvious modifications thereof. In particular, the diesters can be made by acylating an appropriate carboxylic acid ester of formula 9a or 9b.

wherein R', R$_a$ and R$_b$ are as defined above.

Methods of acylating the esters of formula 9a or 9b are known in the art. One method is to treat the ester with a non-nucleophilic strong base to produce the carbanion, then to treat the carbanion with a suitable acylating agent. Suitable strong bases are known in the art, and are discussed with respect to forming the anion of a formula 2 diester above. A preferred base is lithium diisopropylamide. Any conventional acylating agent can be employed. A preferred acylating agent is a reactive halide of a formic acid alkyl ester, as shown in formula 10a and 10b

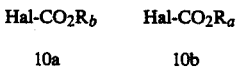

wherein R$_a$ and R$_b$ are as defined above and Hal is chlorine or bromine. In a preferred acylation procedure, an ester of formula 9a or 9b is treated with a base (e.g. lithium diisopropylamide) in an organic solvent (e.g. THF, dimethyl ether, acetonitrile, DMF, DMSO, or dioxane) at a low temperature (e.g. about −30° to −78° C., preferably −65° to −78° C.). The reaction can be allowed to proceed for a period of from 5 minutes to 2 hours, preferably about 1 hour. The acylation reaction can be performed by adding the haloformate ester to the cooled reaction mixture containing the carbanion and allowing the mixture to warm to room temperature. The acylation is allowed to continue for a period of about 4 to 24 hours, preferably 16 hours.

The diesters of formula 2 can be made by an alternative method. In this method, a malonic acid diester of formula 11

wherein $R_a$ and $R_b$ have the meanings given above is alkylated using an alkylating agent of formula 12

wherein R' and Q have the meaning given above. The alkylation is performed in two stages, the first being treatment with a strong base to form the carbanion, that the second being the treatment of the carbanion with the alkylating agent. Methods for carrying out malonic acid ester alkylation are discussed supra and are well known in the art.

The compounds produced by the foregoing processes may be isolated either per se or as acid addition salts thereof. A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with an inorganic acid may be treated with sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The compounds of formula 1 are pharmacologically active, being capable of inhibiting MAO in vitro and in vivo. They are useful for the treatment of psychiatric disorders, in particular depression, which are known to be responsive to MAO inhibitor therapy and are useful in the treatment of Parkinson's syndrome. For the treatment of depression, the compounds can be employed in a manner similar to that of the known clinically active MAO inhibitors, such as phenelzine and tranylcypromine.

Surprisingly, many of the compounds of formula 1 are capable of preferentially inhibiting the B form of MAO in vitro and, at suitable low dosages in vivo, such compounds will inhibit MAO-B without substantially inhibiting MAO-A. At dosage levels where such compounds exert a selective effect on MAO-B, the compounds will not produce a marked "cheese effect". Hence, as with L-deprenyl, a known selective inhibitor of MAO-B, such compounds can be employed at suitable dosages for the treatment of depression, or for the potentiation of L-dopa in the treatment of Parkinsonism, with a significantly decreased risk of producing side effects, such as the "cheese effect".

When employed to treat depression, the effective dosage of the compounds of formula 1 will vary according to the particular compound being employed, the severity and nature of the depression and the particular subject being treated. In general, effective results can be achieved by administering a compound at a dosage level from about 0.1 mg to about 100 mg per day, given systemically. Therapy should be initiated at lower dosages, the dosage thereafter being increased until the desired effect is obtained.

As mentioned above the compounds of formula 1 are also useful for the treatment of Parkinson's syndrome when administered in combination with exogenous dopa, in particular L-dopa and a peripherally acting decarboxylase inhibitor such as carbidopa or benserazide. The coadministration of a compound of formula 1 with L-dopa potentiates the effect of L-dopa and thereby provides effective therapy of Parkinsonism using substantially lower doses of L-dopa resulting in a decrease in side effects. The compounds of formula 1 potentiate L-dopa by preventing the oxidative deamination of dopamine by the monoamine oxidase enzyme in the brain.

In order to potentiate the therapeutic effects of L-dopa in the treatment of Parkinsonism, the dosage of a compound of formula 1 must be effective to block the oxidation of dopamine centrally. The effective dosage will vary according to the particular compound employed, the relative amount of co-administered L-dopa, the route of administration, and the severity of the symptoms being treated. Therapy should be initiated at lower dosages, the dosage thereafter being increased until the desired potentiation of L-dopa is achieved.

When employed to treat Parkinson's syndrome alone, L-dopa is administered initially at a dose of from 0.1 to 1 g daily, after which the amount administered is gradually increased over a 3 to 7 day period to a maximum tolerated daily dose of about 8 grams (given in divided doses). By co-administering a compound of formula 1 with L-dopa, the dosage of L-dopa administered can be reduced 2-10 fold, as compared to the dosage of L-dopa alone. In general, the amount of the compound of formula 1 as compared to the amount of L-dopa administered will vary from about 1:2 to 1:500.

In effecting treatment of Parkinson's syndrome according to the present invention, an effective amount of a fluoroallylamine will generally be from about 0.1 mg/day to about 100 mg/day, an effective amount of exogenous L-dopa will generally be from about 0.01 g/day to about 1.5 g/day, and an effective amount of a peripherally acting decarboxylase inhibitor such as carbidopa or benserazide will generally be from about 10 mg/day to about 200 mg/day.

It will be understood that a compound of formula 1 can be co-administered with L-dopa either substantially at the same time as or prior to the administration of L-dopa. When administered prior, the compound can be given up to 4 hours prior, depending on the route of administration and severity of the condition being treated.

When used in combination with exogenous L-dopa, a compound of formula 1 can be administered in unit dosage form, either in formulations containing the compound as the sole active agent or in formulations containing both the compound and L-dopa as active agents. In either mode of administration, the amount of compound of formula 1 administered as compared to the amount of L-dopa administered, will vary from 1:1 to 1:500, depending upon the compound employed.

At dosage levels set forth above, the compounds of formula 1 will, in general, inhibit both forms of MAO. However, at low dosage levels, they will preferentially inhibit MAO-B and have a decreased risk of producing the "cheese effect". Thus, for example, 2-isobutyl-3-fluoroallylamine, 2-butyl-3-fluoroallylamine or 2-hexyl-3-fluoroallylamine will selectively inhibit MAO-B at a systemic dosage range of about 0.1 mg to about 5 mg per day. At this dosage range, the risk of adverse reaction from the "cheese effect" will be substantially reduced or eliminated.

The active compounds of this invention can be administered in various manners to achieve the desired effect. The compounds can be administered alone or in combination with pharmaceutically acceptable carriers or diluents, the proportion and nature of which are determined by the solubility and chemical properties of the compound selected, the chosen route of administration, and standard pharmaceutical practice. The compounds may be administered orally in solid dosage forms, e.g. capsules, tablets, powders, or in liquid forms, e.g. solutions or suspensions. The compounds may also be injected parenterally in the form of sterile solutions or suspensions. Solid oral forms may contain conventional excipients, for instance, lactose, sucrose, magnesium stearate, resins, and like materials. Liquid oral forms may contain various flavoring, coloring, preserving, stabilizing, solubilizing, or suspending agents. Parenteral preparations are sterile aqueous or non-aqueous solutions or suspensions which may contain certain various preserving, stabilizing, buffering, solubilizing, or suspending agents. If desired, additives, such as saline or glucose may be added to make the solutions isotonic.

The amount of active compound administered will vary and can be any effective amount. Unit doses of these compounds can contain, for example, about 5 mg to about 100 mg of the compounds and may be administered, for example, one or more times daily, as needed.

The term "unit dosage form" is used herein to mean a single or multiple dose form containing a quantity of the active ingredient in admixture with or otherwise in association with the diluent or carrier, and quantity being such that one or more predetermined units are normally required for a single therapeutic administration. In the case of multiple dose forms such as liquids or scored tablets, said predetermined unit will be one fraction such as 5 ml (teaspoon) quantity of a liquid or a half or quarter of a scored tablet, of the multiple dose form.

In the composition aspect of the invention, there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefore. A carrier or diluent may be solid, semi-solid, or liquid material which serves as a vehicle, excipient, or medium for the active ingredient. Suitable diluents or carriers are well known per se. The pharmaceutical formulations may be adapted for enteral or parenteral use and may be administered to the patient in the form of tablets, capsules, suppositories, solutions, suspensions or the like.

The invention is illustrated in the following nonlimiting Examples.

EXAMPLE 1 tert-Butyl 4-Methylvalerate

A solution of 4-methylvaleric acid (25 g) in tert-butyl acetate (538 ml) is treated with perchloric acid (2.7 ml) then stirred at ambient temperature for 1.5 h. This is subsequently poured into water (350 ml) containing NaOH (50 g) and the tert-butyl ester is isolated by ether extraction as a pale yellow oil (24.90 g; 68% yield).

NMR(CDCl$_3$) $\delta$0.88(d, J=6Hz,6H), 1.45 (m, 12H), 2.20 (t, J=7.5 Hz, 2H).

EXAMPLE 2

Ethyl 2-(tert-Butoxycarbonyl)-4-methylvalerate

A solution of lithium diisopropylamide is prepared from diisopropylamine (29.02 g) and 1.6 M n-butyl lithium (183.5 ml) in THF (45 ml). This is cooled to $-78°$ C. and a solution of tert-butyl 4-methylvalerate (24.67 g) in THF (45 ml) is added slowly. After 1 hour a solution of ethyl chloroformate (15.56 g) in THF (45 ml) is added and stirring is continued at ambient temperature for 24 hours. The mixture is then poured into water, neutralized with dilute ageous HCl and the product isolated by ether extraction. In this way the crude malonate is obtained as an orange oil (35.57 g).

NMR(CDCl$_3$) $\delta$ 0.85 to 1.78 (m, 21H), 3.27 (t, J=7.5 Hz, 1H), 4.17 (q, J=7 Hz, 2H).

EXAMPLE 3

Ethyl 2-(tert-Butoxycarbonyl)-2-(difluoromethyl-4-methylvalerate

Solid sodium tert-butoxide (27.73 g) is added to a solution of crude ethyl 2-(tert-butoxycarbonyl)-4-methylvalerate (35.37 g) in THF (300 ml). The mixture is stirred for 1 hour then heated to 45° C. at which time Freon (ClCHF$_2$) gas is added rapidly for about 10 minutes. Stirring is continued for 1 hour under an atmosphere of Freon 22 during which time the temperature falls to ambient. The reaction mixture is poured into water/brine and the crude product is isolated as an orange oil (35.89 g) by ether extraction. NMR(CDCl$_3$) $\delta$ 0.83 to 2.00 (m, 21H), 4.23 (q, J=7 Hz, 2H), 6.23 (t, J=54 Hz, 1H).

EXAMPLE 4

(E)-Ethyl 2-Isobutyl-3-fluoroacrylate

A solution of ethyl 2-(tert-butoxycarbonyl)-2-(difluoromethyl)-4-methylvalerate (35.68 g) in trifluoroacetic acid (243 ml) is stirred for 1 hour, then the excess trifluoroacetic acid is removed by evaporation. The residual oil (30.89 g) is dissolved in THF (400 ml) and treated slowly with M NaOH (121 ml) so that the pH does not rise above 7.02. After completion of the addition the solution is stirred for another 15 minutes and the product is extracted into ether. Careful distillation at atmospheric pressure, then at 24 mm allows the separation of essentially pure acrylate as a colorless oil (5.72 g), bp 70°–72° C.

NMR(CDCl$_3$) $\delta$ 0.90 (d, J=6 Hz , 6H), 1.27 (t, J=7 Hz, 3H) 1.37 to 2.30 (m, 3H), 4.18 (q, J=7 Hz, 2H), 7.57 (d, J=83 Hz, 1H).

EXAMPLE 5

(E)-2-Isobutyl-3-fluoroallyl Alcohol

A solution of the acrylate (5.60 g) in hexane (172 ml) cooled to $-10°$ C. is treated slowly with a solution of diisobutylaluminum hydride in hexane (1M solution, 96.5 ml). The solution is stirred at ambient temperature for 90 minutes, then cooled to 10° C. and treated consecutively with CH$_3$OH (96.5 ml) and 6M aqueous HCl (138 ml). Water is added and the product is isolated by ether extraction followed by careful distillation of the solvents to leave almost pure alcohol (7.0 g) contaminated with some residual hexane.

NMR(CDCl$_3$) δ 0.93 (d, J=6 Hz, 6H) 1.45 to 2.17 (m, 3H), 2.03 (s, 1H), 3.98 (d, J=4Hz, 2H), 6.67 (d, J=85 Hz, 1H).

EXAMPLE 6

(E)-1-Fluoro-2-isobutyl-3-phthalimidopropene

A solution of the crude alcohol (7.0 g), potassium phthalimide (4.41 g) and triphenylphosphine (7.80 g) in THF (200 ml) is cooled to 0° C. and treated slowly with a solution of diethyl azodicarboxylate (5.22 g) in THF (70 ml). Stirring is continued at ambient temperature overnight, then the solution is evaporated to leave an orange paste (15 g). Chromatography on silica (20% ether in petroleum ether as eluant) allows the separation of pure phthalimide (4.25 g), mp 57°-60° C.

NMR(CDCl$_3$) δ 0.92 (m,6H), 1.95 (m, 3H), 4.13 (d.d, J=3.5 Hz, 1.0 Hz, 2H), 6.78 (d, J=84 Hz, 1H), 7.80 (m, 4H).

EXAMPLE 7

(E)-2-Isobutyl-3-fluoroallylamine

A mixture of the phthalimide (3.75 g) and hydrazine hydrate (1.08 g) in ethanol (250 ml) is refluxed for 2.5 hours. 6N aqueous HCl (12.5 ml) is added and the mixture is evaporated to dryness. The residue is dissolved in water (50 ml), the pH is adjusted to 8 with NaHCO$_3$, then a solution of di-tert-butyl dicarbonate (4.68 g) in chloroform (500 ml) is added. The mixture is refluxed for 2.5 hours then the crude N-Boc derivative is isolated by CHCl$_3$ extraction. Purification is achieved by silica chromatography (40% methylene chloride in petroleum ether) whereupon pure material (1.20 g) is obtained as an almost colorless oil. This is dissolved in hydrogen chloride-saturated ether (25 ml), left overnight, then filtered to give the hydrochloride salt of (E)-2-isobutyl-3-fluoroallylamine (0.46 g) as colorless plates; mp 179° C.

Analysis for C$_7$H$_{14}$FN.HCl: Found: C, 50.34, H, 8.87, N, 8.35%. Require: C, 50.15; H, 9.01, N, 8.35%.

NMR(D$_2$O) δ 0.80 (d, J=7 Hz, 6H); 1.50 to 2.10 (m, 3H); 3.44 (broadened s, 2H); 6.80 (d, J=83 Hz, 1H).

According to this procedure the following compounds are prepared. In each case, the allylamine is reported as its hydrochloride salt.

(E)-2-Isopropyl-3-fluoroallylamine, prepared form isovaleric acid;

(E)-2-sec-Butyl-3-fluoroallylamine, prepared from 3methylvaleric acid; mp 236° C.

Analysis for C$_7$H$_{14}$FN.HCl: Found: C, 49.65; H, 8.72; N, 8.64%. Require: C, 50.15; H, 9.01; N, 8.35%.

(E)-2-Butyl-3-fluoroallylamine, prepared from hexanoic acid; mp 141° C.

Analysis for C$_7$H$_{14}$FN.HCl: Found: C, 50.17; H, 8.78; N, 8.31%. Require: C, 50.15; H, 9.01; N, 8.35%.

(E)-2-Hexyl-3-fluoroallylamine, prepared from octanoic acid; p 141° C.

Analysis for C$_9$H$_{18}$FN.HCl Found: C, 55.24; H, 9.00; N, 7.08% . Require: C, 55.23; H, 9.27; N, 7.15%.

(E)-2-Heptyl-3-fluoroallylamine, prepared from nonanoic acid; mp 129° C.

Analysis for C$_{10}$H$_{20}$FN.HCl: Found: C, 57.11; H, 9.70; N, 7.11%. Require: C, 57.27; H, 10.09; N, 6.67%.

EXAMPLE 8

Ethyl 2-tert-Butoxycarbonyl)tridecanoate

A suspension of pentane-washed sodium hydride (4.36 g of a 50% oil dispersion) and tert-butyl, ethyl malonate (18.83 g) in THF (150 ml) is stirred at ambient temperature for 15 minutes, then cooled in an ice-salt bath. A solution of undecyl bromide (23.52 g) in THF (50 ml) is added and stirring is continued in the cold for 1 hour, then overnight at ambient temperature. Ether extraction is followed by distillation of remaining starting materials whereupon the residue is found to consist of the desired malonate with a small amount of dialkylated material.

EXAMPLE 9

(E)-2-Undecyl-3-fluoroallylamine

Ethyl 2-(tert-butoxycarbonyl)tridecanoate is converted to the allylamine by following the procedure of Examples 3, 4, 5, 6 and 7, mp. 140° C.

Analysis for C$_{14}$H$_{28}$FN.HCl Found: C, 63.17; H, 10.75; N, 5.25% . Require: C, 63.25; H, 11.00; N, 5.27%.

NMR(D$_2$O) δ 0.80 (m, 3H), 1.3 (m, 18H), 2.20 (m, 2H), 3.50 (d, J=3 Hz, 2H), 6.93 (d, J=82 Hz, 1H).

EXAMPLE 10

(Z)-2-Isopropoxymethyl-3-fluoroallylamine

Solid 1-fluoro-2-bromomethyl-3-phthalimidopropene (0.60 g) is added to a previously prepared mixture of isopropanol (0.12 g) and sodium hydride dispersion (96 mg of 55–60% oil dispersion) in dimethylformamide (10 ml) at room temperature. Stirring is continued for 3 hours, then brine as added and the product is isolated by ether extraction. This product is treated with hydrazine hydrate (0.13 g) in ethanol (20 ml) under reflux for 3 hours. Dilute aqueous hydrochloric acid is added and the resulting mixture is washed with ethyl acetate, then the aqueous layer is concentrated to about 5 ml. The residual solution is treated with di-tert-butyl dicarbonate (0.44 g), sodium chloride (1 g) and chloroform (20 ml) then sufficient sodium bicarbonate is added to adjust the pH of the aqueous layer to about 8. The mixture is refluxed for 1½ hours then the crude N-Boc derivative can be isolated by extractive work-up. Purification is achieved by silica chromatography using ether/petroleum ether as eluent. Cleavage of the Boc protecting group (anhydrous hydrogen chloride in ether) affords (Z)-2-isopropoxymethyl-3fluoroallylamine as its hydrochloride salt.

EXAMPLE 11

(Z)-2-Thiopropoxymethyl-3-fluoroallylamine

Following the procedure described in Example 10 but replacing isopropanol with 1-propanethiol, (Z)-2-thiopropoxymethyl-3-fluoroallylamine is obtained as its hydrochloride salt.

EXAMPLE 12

Inhibition of MAO—In Vitro Testing

The ability of a compound of structure 1 to inhibit MAO can be determined in vitro by the method of A. Christmas et al., Br. J. Pharmacol 45, 490 (1972) in partially purified mitochondria from rat brain using $^{14}$C p-tyramine Or $^{14}$C phenethylamine and $^{14}$C 5-HT as the substrate. The MAO inhibitory activity of a compound is expressed as the "IC$_{50}$" value, which is the molar concentration required to produce 50% inhibition of the enzyme. The IC$_{50}$values for certain compounds of structure 1 were determined using the above-described method, and the results are set forth in Table 1.

The selectivity of a compound of structure 1 with respect to inhibition of MAO-A and MAO-B can be determined by preparing mitochondria from rat brain by homogenation in phosphate buffer (0.1 M, pH 7.2) followed by differential centrifugation. The mitochondria are suspended in the same buffer, the test compound is added at the desired concentration, and the system is incubated. At different time intervals, aliquots are taken and MAO activity is measured using $^{15}C$ 5-hydroxytryptamine (5HT; a preferred substrate for MAO-A) or $^{14}C$-phenethylamine (PEA; a preferred substrate for MAO-B) as the substrates. The selectivity is expressed as the ratio of the inhibitory activity against MAO-B versus the inhibitory activity against MAO-A. (Zreika, McDonald, Bey, Palfreyman, J. Neurochem., 43, 448–454 (1984)).

The data shown in Table I demonstrates that the compounds tested are potent irreversible inhibitors of MAO and that many of the compounds are highly selective for MAO-B.

TABLE I

| TEST COMPOUND | IC$_{50}$(M) PEA | 5HT | MAO-B SELECTIVITY |
|---|---|---|---|
| (E)-2-Isobutyl-3-fluoroallylamine | $3 \times 10^{-8}$ | $2.3 \times 10^{-6}$ | 77 |
| (E)-2-Butyl-3-fluoroallylamine | $2 \times 10^{-9}$ | $1.1 \times 10^{-7}$ | 55 |
| (E)-2-Hexyl-3-fluoroallylamine | $7 \times 10^{-9}$ | $1.7 \times 10^{-7}$ | 24 |
| (E)-2-Heptyl-3-fluoroallylamine | $4.5 \times 10^{-9}$ | $6 \times 10^{-8}$ | 13 |
| (E)-2-Isopropyl-3-fluoroallylamine | $2.5 \times 10^{-6}$ | $1.7 \times 10^{-4}$ | 68 |
| (E)-2-sec-Butyl-3-fluoroallylamine | $7 \times 10^{-6}$ | $1.7 \times 10^{-4}$ | 24 |
| (E)-2-Undecyl-3-fluoroallylamine | $5 \times 10^{-7}$ | $7.5 \times 10^{-7}$ | 1.5 |

EXAMPLE 13

Inhibition of MAO-Ex vivo

The ability of a compound of formula 1 to inhibit MAO can be determined ex vivo by the following procedure:

The test compound is administered orally (po) to rats and the animals are killed at various times after treatment. The brain is removed and a mitochondrial fraction, described in Example 12 is prepared. MAO activity is determined using $^{14}C$ p-tyramine, as the substrate. Selectivity can be determined by repeating the above-described test using either $^{14}C$ 5-hydroxytryptamine (for MAO-A) or $^{14}C$ phenethylamine (for MAO-B) as the substrate for determining the % inhibition.

When (E)-2-isobutyl-3-fluoroallylamine is tested in this way the ED$_{50}$is 0.05 mg/kg for MAO-B inhibition and 0.8 mg/kg for MAO-A inhibition.

EXAMPLE 14

An illustration composition of hard gelatin capsules is as follows:

| (a) Active compound | 5 mg |
|---|---|
| (b) Talc | 5 mg |
| (c) Lactose | 90 mg |

The formulation is prepared by passing the dry powders of (a) and (b) through a fine mesh screen and mixing them well. The powder is then filled into hard gelatin capsules at a net fill of 100 mg per capsule.

EXAMPLE 15

An illustrative composition for tablets is as follows:

| (a) Active compound | 5 mg |
|---|---|
| (b) Starch | 45 mg |
| (c) Lactose | 48 mg |
| (d) Magnesium stearate | 2 mg |

The granulation obtained upon mixing the lactose with the compound (a) and the part of the starch and granulated with starch paste is dried, screened, and mixed with the magnesium stearate. The mixture is compressed into tablets weighing 100 mg each.

EXAMPLE 16

An illustrative composition for an injectable suspension is the following 1 ml ampule for an intramuscular injection.

| (a) Active compound | 0.5 |
|---|---|
| (b) Polyvinylpyrrolidone | 0.5 |
| (c) Lecithin | 0.25 |
| (d) Water from injection to make | 100.00 |

The materials (a)–(d) are mixed, homogenized, and filled into 1 ml ampules which are sealed and autoclaved minutes at 121° C. Each ampule contains 5 mg per ml of the active compound.

We claim:

1. A method of treating Parkinson's syndrome in a patient in need thereof which comprises conjunctive administration to said patient of a fluoroallylamine of the formula

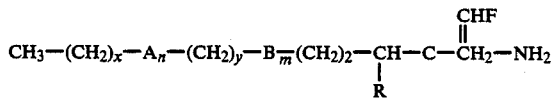

wherein
R is hydrogen or a (C$_1$–C$_4$) alkyl;
n and m are each either zero or 1;
A and B are each selected from

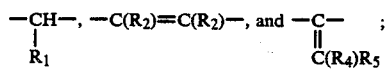

x+y+z is zero or an integer of from 1 to 16;
R$_1$, R$_2$, R$_3$, R$_4$, and R$_5$ are each a hydrogen or a (C$_1$–C$_4$)alkyl,
or a pharmaceutically acceptable acid addition salt thereof, exogenous L-dopa, and a peripherally acting aromatic amino acid decarboxylase inhibitor, each in amounts which when conjunctively administered are effective to treat Parkinson's syndrome.

2. A method of claim 1 wherein n and m are both zero.

3. A method of claim 1 wherein A or B is

4. A method of claim 2 wherein x+y+z is zero to 4.

5. A method of claim 4 wherein R is hydrogen or methyl.

6. A method of claim 1 wherein R is hydrogen, n is 1 and m is zero, A is

x+y+z is zero and $R_1$ is methyl, that is the compound 2-isobutyl-3-fluoroallylamine.

7. A method of claim 6 wherein the fluoroallylamine is (E)-2-isobutyl3-fluoroallylamine.

8. A method of any one of claims 1 and 2 through 7 in which the decarboxylase inhibitor is carbidopa.

9. A method of any one of claims 1 and 2 through 7 in which the decarboxylase inhibitor is benserazide.

* * * * *

UNITED STATES PATENT AND TRADEMARK OFFICE
CERTIFICATE OF CORRECTION

PATENT NO. : 4,916,151

DATED : April 10, 1990

INVENTOR(S) : Philippe Bey et al.

It is certified that error appears in the above-identified patent and that said Letters Patent is hereby corrected as shown below:

Column 3, Line 66 patent reads: "$x+y+z$" and should read: --O, S, and $SO_2$; and $x+y+z$--.

Signed and Sealed this

First Day of October, 1991

Attest:

HARRY F. MANBECK, JR.

Attesting Officer     Commissioner of Patents and Trademarks